United States Patent
Frey et al.

(10) Patent No.: US 9,434,675 B2
(45) Date of Patent: *Sep. 6, 2016

(54) METHOD FOR PRODUCING ISONONANOIC ACID ESTERS, STARTING FROM 2-ETHYL HEXANOL

(71) Applicant: Oxea GmbH, Oberhausen (DE)

(72) Inventors: Guido D. Frey, Riedstadt (DE); Matthias Eisenacher, Wesel (DE); Kristina Kockrick, Düsseldorf (DE); Heinz Strutz, Moers (DE)

(73) Assignee: OXGA GMBH, Oberhausen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/413,550

(22) PCT Filed: Jun. 18, 2013

(86) PCT No.: PCT/EP2013/001797
§ 371 (c)(1),
(2) Date: Jan. 8, 2015

(87) PCT Pub. No.: WO2014/008974
PCT Pub. Date: Jan. 16, 2014

(65) Prior Publication Data
US 2015/0158805 A1    Jun. 11, 2015

(30) Foreign Application Priority Data

Jul. 13, 2012  (DE) ........................ 10 2012 013 968

(51) Int. Cl.
| | |
|---|---|
| C07C 67/08 | (2006.01) |
| C07C 1/24 | (2006.01) |
| C07C 45/50 | (2006.01) |
| C07C 51/235 | (2006.01) |
| C10M 129/70 | (2006.01) |
| C10M 129/74 | (2006.01) |
| C07C 29/48 | (2006.01) |
| C08K 5/103 | (2006.01) |
| C08K 5/10 | (2006.01) |

(52) U.S. Cl.
CPC ............... *C07C 67/08* (2013.01); *C07C 1/24* (2013.01); *C07C 29/48* (2013.01); *C07C 45/50* (2013.01); *C07C 51/235* (2013.01); *C08K 5/103* (2013.01); *C10M 129/70* (2013.01); *C10M 129/74* (2013.01); *C07C 2521/04* (2013.01); *C08K 5/10* (2013.01); *C10M 2207/281* (2013.01); *C10M 2207/283* (2013.01)

(58) Field of Classification Search
CPC ......... C07C 67/08; C07C 1/24; C07C 45/50; C07C 51/235; C07C 11/02; C07C 47/02; C07C 53/126; C07C 69/28; C07C 69/30; C07C 69/33; C07C 2521/04; C07C 29/48; C08K 5/10; C08K 5/103; C10M 129/70; C10M 129/74; C10M 2207/281; C10M 2207/283
USPC ........... 106/505; 508/463; 524/315; 560/174
See application file for complete search history.

(56) References Cited

U.S. PATENT DOCUMENTS

| | | | |
|---|---|---|---|
| 2,468,764 | A | 5/1949 | Laurent |
| 2,871,248 | A | 1/1959 | Kirkand et al. |
| 2,919,973 | A | 1/1960 | Stillwell et al. |
| 3,527,809 | A | 9/1970 | Pruett et al. |
| 4,148,830 | A | 4/1979 | Pruett et al. |
| 4,222,966 | A | 9/1980 | Bexten et al. |
| 4,247,486 | A | 1/1981 | Brewester et al. |
| 4,283,562 | A | 8/1981 | Billig et al. |
| 6,228,820 | B1 | 5/2001 | Sakai et al. |
| 6,281,372 | B1 | 8/2001 | Wiese et al. |
| 6,423,856 | B1 | 7/2002 | Springer et al. |
| 6,617,289 | B2 | 9/2003 | Memita et al. |
| 7,799,945 | B2 | 9/2010 | Springer |
| 8,399,697 | B2 | 3/2013 | Weber et al. |
| 8,524,938 | B2 | 9/2013 | Frey et al. |

(Continued)

FOREIGN PATENT DOCUMENTS

| | | |
|---|---|---|
| CA | 1081254 A1 | 7/1980 |
| DE | 950007 C | 10/1956 |

(Continued)

OTHER PUBLICATIONS

International Preliminary Report on Patentability dated Jan. 15, 2015.

(Continued)

*Primary Examiner* — Jafar Parsa
*Assistant Examiner* — Amy C Bonaparte
(74) *Attorney, Agent, or Firm* — Michael W. Ferrell

(57) ABSTRACT

A Process for preparing carboxylic esters of a mixture of structurally branched C9 monocarboxylic acids proceeding from 2-ethylhexanol is characterized in that (a) 2-ethylhexanol is dehydrated to an octene mixture in the presence of a catalyst;
(b) the octene mixture obtained in step a) is reacted in the presence of a transition metal compound of group VIII of the periodic table of the elements with carbon monoxide and hydrogen to give a mixture of isomeric isononanals;
(c) the mixture of isomeric isononanals obtained in step b) is oxidized to a mixture of structurally branched C9 monocarboxylic acids; and
(d) the mixture of structurally branched C9 monocarboxylic acids obtained in step c) is reacted with alcohols to give carboxylic esters.

17 Claims, No Drawings

(56) References Cited

U.S. PATENT DOCUMENTS

| | | | | |
|---|---|---|---|---|
| 2003/0078453 | A1* | 4/2003 | Springer | C07C 51/235 562/534 |
| 2004/0238787 | A1* | 12/2004 | Wiese | C07C 69/80 252/182.28 |
| 2011/0087046 | A1* | 4/2011 | Frey | C07C 67/08 560/183 |
| 2015/0191410 | A1* | 7/2015 | Frey | C07C 1/24 549/515 |

FOREIGN PATENT DOCUMENTS

| | | |
|---|---|---|
| DE | 2604545 A1 | 8/1977 |
| DE | 2737633 B1 | 2/1979 |
| DE | 19908320 A1 | 8/2000 |
| DE | 19940991 A1 | 3/2001 |
| DE | 10010771 C1 | 5/2001 |
| DE | 102009048771 A1 | 4/2011 |
| EP | 0475751 A1 | 3/1992 |
| EP | 0903335 A1 | 3/1999 |
| EP | 1199300 A2 | 4/2002 |
| EP | 1281701 A1 | 2/2003 |
| EP | 1854778 A1 | 11/2007 |
| EP | 2308821 A2 | 4/2011 |
| GB | 313426 A | 6/1929 |
| WO | 9012849 A1 | 11/1990 |
| WO | 9519389 A1 | 7/1995 |
| WO | 03029180 A1 | 4/2003 |

OTHER PUBLICATIONS

International Search Report dated Oct. 10, 2013.
Scharfe, G., "Convert butenes to high octane oligomers", Hydrocarbon Processing, Apr. 1973, pp. 171-173.

* cited by examiner

METHOD FOR PRODUCING ISONONANOIC ACID ESTERS, STARTING FROM 2-ETHYL HEXANOL

CLAIM FOR PRIORITY

This application is a national phase application of PCT/EP2013/001797 FILED Jun. 18, 2013 which was based on application DE 10 2012 013 968.3 FILED Jul. 13, 2012. The priorities of PCT/EP2013/001797 and DE 10 2012 013 968.3 are hereby claimed and their disclosures incorporated herein by reference.

TECHNICAL FIELD

The present invention relates to the preparation of carboxylic esters of a mixture of structurally branched C9 monocarboxylic acids by dehydration of 2-ethylhexanol, hydroformylation of the octene mixture obtained to a mixture of isomeric isononanals, subsequent oxidation to the corresponding isononanoic acids and esterification with alcohols, to carboxylic esters of triethylene glycol, neopentyl glycol and 1,3-butanediol of said mixture, and to the use thereof.

BACKGROUND

Isononanoic acid, a mixture of structurally branched C9 monocarboxylic acids, is an important intermediate in industrial organic chemistry which is processed to give a multitude of conversion products for a wide variety of different fields of use. For example, the salts thereof are used as drying accelerators or siccatives for coatings.

Isononanoic acid is processed further in large volumes to give carboxylic esters which find use as lubricant. Particularly esterification with polyhydric alcohols such as neopentyl glycol, trimethylolpropane, ditrimethylolpropane, pentaerythritol or dipentaerythritol gives lubricants which are used in the operation of refrigerators. Isononanoic acid is frequently esterified in a mixture with other $C_4$-$C_{12}$-monocarboxylic acids such as 2-methylbutyric acid, n-pentanoic acid, n-heptanoic acid, 2-ethylhexanoic acid or n-octanoic acid (EP 1 281 701 A1, EP 1 199 300 A2, EP 0 903 335 A1, EP 0 475 751 A1, WO 90/12849 A1).

Esters of isononanoic acid are likewise used as plasticizers for thermoplastic polymers. Plasticizers for PVC based on isononanoic acid with polyols are described, for example, in WO 95/19389 A1. A specific class of ester plasticizers, which are also abbreviated to the term G esters, contains ether diols such as diethylene glycol, triethylene glycol or tetraethylene glycol as the alcohol component. They are utilized for plasticization of polyvinyl butyral films which are used as the intermediate layer in the production of multilayer or composite glasses. They can likewise be used as coalescence agents or film-forming aids in aqueous dispersions of polymers which find various uses as coating materials (DE 10 2009 048 771 A1, DE 199 40 991 A1). According to EP 2 308 821 A2, the crude esterification product is treated with ozone and ozone-containing gases to lighten the colour, and immediately thereafter subjected to a steam treatment.

For said uses, predominantly an isononanoic acid containing the structurally isomeric form 3,5,5-trimethylhexanoic acid as the main constituent is used. The C-9 hydrocarbon skeleton 3,5,5-trimethylhexyl is based on the petrochemical precursor isobutene, which is dimerized in the presence of acidic catalysts to give diisobutene and is separated by distillation from the higher oligomers likewise formed (Hydrocarbon Processing, April 1973, pages 171-173; Ullmann's Encyclopedia of Industrial Chemistry, 6th Ed., 2003, Vol. 6, page 3). Diisobutene consists essentially of the isomeric octenes 2,4,4-trimethyl-1-pentene and 2,4,4-trimethyl-2-pentene and can be converted to the corresponding aldehyde 3,5,5-trimethylhexanal by the oxo process or hydroformylation reaction with carbon monoxide and hydrogen in the presence of rhodium or cobalt catalysts (Ullmann's Encyclopedia of Industrial Chemistry, 6th Ed., 2003, Vol. 2, page 68, 75; DE 2737633 A). Further C9 isomers present in small amounts are 3,4,4- and 3,4,5-trimethylhexanal, and also 2,5,5-trimethylhexanal, 4,5,5-trimethylhexanal and 6,6-dimethylheptanal. Oxidation of this aldehyde mixture gives an industrially available isononanoic acid typically having a content of 3,5,5-trimethylhexanoic acid of about 90% (Ullmanns Encyklopädie der technischen Chemie, 4th Edition, 1975, Verlag Chemie, Volume 9, pages 143-145; EP 1 854 778 A1). According to DE 199 08 320 A1, dibutene which is separated from an oligomerized butene material is converted through hydrocarboxylation or through hydroformylation with subsequent oxidation to a mixture of isomeric C9 monocarboxylic acids, which is subsequently converted to vinyl esters. These vinyl esters can be used as plasticizers.

The most important raw material source for isobutene is the C4 cut from the steamcracking of naphtha. The availability thereof compared to the C2 and C3 cracking products can be controlled by the conditions of steamcracking and is guided by the market conditions. 1,3-Butadiene is first removed from the C4 cracking products by extraction or by selective hydrogenation to n-butenes. The resulting C4 raffinate, also called raffinate I, comprises predominantly the unsaturated butenes isobutene, 1-butene and 2-butene, and the hydrogenated products n-butane and isobutane. Isobutene is removed from the raffinate I in the next step, and the resulting isobutene-free C4 mixture is referred to as raffinate II.

For the isobutene removal, various processes are employed in industrial production, in which the highest reactivity of the isobutene in relative terms in the raffinate I is exploited. A known method is the reversible proton-catalysed addition of water to give tert-butanol, or methanol addition to give methyl tert-butyl ether. Isobutene can be recovered again from these addition products by redissociation (Weissermel, Arpe, Industrielle Organische Chemie [Industrial Organic Chemisty], VCH Verlagsgesellschaft, 3rd Edition, 1988, p. 74-79).

It is likewise possible to contact the butadiene-free C4 raffinate at elevated temperature and under pressure with an acidic suspended ion exchanger. Isobutene oligomerizes to diisobutene, triisobutene, and in a small portion to higher oligomers. The oligomers are separated from the unreacted C4 compounds. It is then possible to obtain diisobutene or triisobutene in pure form by distillation from the oligomer. The dimerization of n-butenes with isobutene forms the co-dimer to a small degree (Weissermel, Arpe, Industrielle Organische Chemie, VCH Verlagsgesellschaft, 3rd Edition, 1988, p. 77; Hydrocarbon Processing, April 1973, p. 171-173).

Against the background that the availability of octenes based on the C4 cut from naphtha cracking is limited and depends on the local conditions, it is desirable to develop further octene sources based on inexpensively available large-scale products which can be transported to various sites in a simple manner.

2-Ethylhexanol is available inexpensively as an industrial large-scale product which can be sold widely without any problems. As is well known, 2-ethylhexanol is prepared on the industrial scale by hydroformylation or oxo process using propylene to give n-butyraldehyde with subsequent alkali-catalysed aldol condensation to give 2-ethylhexenal followed by full hydrogenation to give 2-ethylhexanol (Ullmann's Encyclopedia of Industrial Chemistry, 7th Edition, 2011, Wiley, Volume 13, pages 579-584).

WO 03/029180 A1 briefly discusses the use of 2-ethylhexanol for preparation of an octene mixture which is processed via dehydration, hydroformylation and hydrogenation to give an isononanol mixture. The emphasis is on the adjustment of the viscosity of the isomeric dialkyl phthalates which are obtained by esterification of isomeric nonanols with phthalic acid or phthalic anhydride. No pointers are given to convert the dehydration products of 2-ethylhexanol to isononanoic acid or isononanoic esters.

The utilization of 2-ethylhexanol as the octene source enables the provision of isononanoic acid based on propylene, and reduces dependence on octene availability based on butene. An isononanoic acid prepared in this way can then be processed further to give carboxylic esters.

SUMMARY OF INVENTION

The present invention therefore consists in a process for preparing carboxylic esters of isononanoic acid proceeding from 2-ethylhexanol. The process is characterized in that
(a) 2-ethylhexanol is dehydrated to octene in the presence of a catalyst;
(b) the octene obtained in step a) is reacted in the presence of a transition metal compound of group VIII of the periodic table of the elements with carbon monoxide and hydrogen to give isononanal;
(c) the isononanal obtained in step b) is oxidized to isononanoic acid; and
(d) the isononanoic acid obtained in step c) is reacted with alcohols to give carboxylic esters.

The present invention likewise relates to carboxylic esters obtainable by
(a) dehydrating 2-ethylhexanol in the presence of a catalyst to octene;
(b) reacting the octene obtained in step a) in the presence of a transition metal compound of group VIII of the periodic table of the elements with carbon monoxide and hydrogen to give isononanal;
(c) oxidizing the isononanal obtained in step b) to isononanoic acid; and
(d) reacting the isononanoic acid obtained in step c) with alcohols to give carboxylic esters.

DETAILED DESCRIPTION

The dehydration of 2-ethylhexanol can be performed either in the liquid phase or in the gas phase over a catalyst suitable therefor. Preference is given to dehydrating in the gas phase at temperatures in the range from 200 to 450° C., preferably from 250 to 380° C., using reactors customary in the art, in the presence of heterogeneous catalysts having dehydrating properties, such as alumina in its various polymorphs, nickel precipitated on alumina, or phosphoric acid precipitated on silica or alumina. Such heterogeneous catalysts suitable for dehydration are known from the prior art (GB 313426, U.S. Pat. No. 2,468,764, U.S. Pat. No. 2,919,973) and are commercially available, for example, as Al3996 from BASF SE. U.S. Pat. No. 2,919,973 discusses the dehydration of 2-ethylhexanol over a heterogeneous alumina catalyst at temperatures around 350° C. and at a catalyst hourly space velocity of 2.4 to 2.8 liters of 2-ethylhexanol per liter of catalyst and hour. However, the prior art does not give any information regarding the isomer distribution in the octene mixture obtained.

The reactor used in the process according to the invention for the dehydration of 2-ethylhexanol may, as well as the catalyst bed, also contain further random packings or internals, for example Raschig rings, saddles, Pall rings, filter plates or column trays. If random packings are used, they are preferably positioned above the catalyst bed in order to reduce the dead volume. If dehydration is effected in the liquid phase, it is possible to dispense with stirrer apparatus, internals and random packings, such that only the dehydration catalyst is present in the reaction vessel.

In a preferred mode of operation, 2-ethylhexanol is heated in an upstream vaporizer and conducted in gaseous form over the catalyst bed, optionally using an inert carrier gas such as nitrogen, carbon dioxide or noble gases. The space velocity V/Vh of the heterogeneous catalyst may vary over a wide range and is generally from 0.2 to 3.5 liters of 2-ethylhexanol per liter of catalyst an hour. The reaction mixture withdrawn from the dehydration zone is subsequently condensed. As a result of the water eliminated, an aqueous phase is obtained, which is separated from the organic olefin phase by simple phase separation. The octene obtained is a mixture of structurally isomeric octenes with the singly branched octenes 2-ethyl-1-hexene and cis/trans-3-methyl-3-heptene and cis/trans-3-methyl-2-heptene as main components. No significant amounts of di-C8-ethers are formed.

The octene present after removal of the splitting water is subsequently used without further purification, or appropriately after distillative purification, for the reaction with carbon monoxide and hydrogen in the hydroformylation reaction or oxo process. The mixture of carbon monoxide and hydrogen used is also referred to as synthesis gas. The hydroformylation reaction is performed in a homogeneous reaction system. The term "homogeneous reaction system" represents a homogeneous solution composed essentially of solvent, if added, catalyst, olefinically unsaturated compound and reaction product. Particularly effective solvents have been found to be the higher-boiling condensation compounds of the aldehydes to be prepared, especially the trimers of the aldehydes to be prepared, which are obtained as by-products in the hydroformylation, and mixtures thereof with the isononanal to be prepared, and so a further addition of solvent is not absolutely necessary. In some cases, however, an addition of solvent may be found to be appropriate. The solvents used are organic compounds in which starting material, reaction product and catalyst are soluble. Examples of such compounds are aromatic hydrocarbons such as benzene and toluene or the isomeric xylenes and mesitylene. Other commonly used solvents are paraffin oil, cyclohexane, n-hexane, n-heptane or n-octane, ethers such as tetrahydrofuran, ketones, or Texanol® from Eastman. The proportion of the solvent in the reaction medium can be varied over a wide range and is typically between 20 and 90% by weight, preferably 50 to 80% by weight, based on the reaction mixture. The hydroformylation of the octene can also be effected without addition of solvent. The hydroformylation reaction is typically performed in homogeneous organic phase in the presence of at least one transition metal compound of group VIII of the periodic table of the elements. The reaction can be performed either in the presence or in the absence of complex-forming organoelemental compounds which act as complex ligands.

If the hydroformylation reaction is performed in the presence of complex ligands, the use of organophosphorus compounds as organoelemental compounds is suitable. Such complexes and the preparation thereof are known (U.S. Pat. No. 3,527,809 A, U.S. Pat. No. 4,148,830 A, U.S. Pat. No. 4,247,486 A, U.S. Pat. No. 4,283,562 A). They can be used as single complexes or else as a mixture of different complexes. The transition metal concentration in the reaction medium extends over a wide range from about 1 to about 1000 ppm by weight and is preferably 10 to 700 ppm by weight and especially 25 to 500 ppm by weight, based in each case on the homogeneous reaction mixture. The catalyst used may be the transition metal complex of stoichiometric composition. However, it has been found to be appropriate to perform the hydroformylation in the presence of a catalyst system composed of transition metal complex and free complex ligand which does not enter into a complex with the transition metal. The free complex ligand may be the same as in the transition metal complex, but it is also possible to use different complex ligands. The preferred complex ligands include triarylphosphines such as triphenylphosphine, trialkylphosphines such as tri(cyclohexyl) phosphine, alkylphenylphosphines, organic phosphites or diphosphites. The molar ratio of transition metal to complex ligand is generally 1:1 to 1:1000, but it may also be higher. Preference is given to using the transition metal and the complex ligand in a molar ratio of 1:3 to 1:500 and especially of 1:50 to 1:300. The hydroformylation reaction in the presence of complex ligands is frequently also referred to as the modified variant, which is typically performed at temperatures of 50 to 180° C., preferably of 100 to 160° C. and total pressures of 0.2 to 30 M Pa, preferably of 1 to 20 M Pa.

The hydroformylation reaction can likewise be performed in the absence of complex ligands according to the unmodified variant. Such transition metal catalysts, for example not modified with phosphines or phosphites, and the suitability thereof as a catalyst for hydroformylation are known from the literature, and they are referred to as unmodified transition metal catalysts. It is assumed in the specialist literature that the transition metal compound $HM(CO)_4$ is the catalytically active transition metal species in the case of unmodified transition metal catalysis, even though this has not been demonstrated clearly owing to the many chemisms which run alongside one another in the reaction zone.

The transition metals of group VIII of the periodic table of the elements used are preferably cobalt, rhodium, iridium, nickel, palladium, platinum, iron or ruthenium, and especially cobalt or rhodium. The modified or unmodified transition metal catalyst forms under the conditions of the hydroformylation reaction from the transition metal compounds used, such as salts thereof, such as chlorides, nitrates, sulphates, acetates, pentanoates, 2-ethylhexanoates or isononanoates, the chalcogenides thereof, such as oxides or sulphides, the carbonyl compounds thereof, such as $M_2(CO)_8$, $M_4(CO)_{12}$, $M_6(CO)_{16}$, $M_2(CO)_9$, $M_3(CO)_{12}$, the organo-transition metal compounds thereof, such as carbonyl acetylacetonates or cyclooctadienyl acetates or chlorides, in the presence of carbon monoxide/hydrogen mixtures. The transition metal compound can be used in solid form or appropriately in solution. Suitable transition metal compounds for use as a catalyst precursor are especially rhodium isononanoate, rhodium acetate, rhodium 2-ethylhexanoate or cobalt isononanoate, cobalt acetate or cobalt 2-ethylhexanoate, or $Co_2(CO)_8$, $Co_4(CO)_{12}$, $Rh_2(CO)_8$, $Rh_4(CO)_{12}$ or $Rh_6(CO)_{16}$ or cyclopentadienyl-rhodium compounds, rhodium acetylacetonate or rhodium dicarbonyl acetylacetonate. Preference is given to using rhodium oxide and especially rhodium acetate, rhodium 2-ethylhexanoate and rhodium isononanoate.

It is also possible first to preform the transition metal catalyst in a precarbonylation stage and then to feed it to the actual hydroformylation stage. The preforming conditions correspond generally to the hydroformylation conditions.

Since the use of transition metal catalysts unmodified with complex ligands generally requires a lower transition metal content, in the unmodified variant, generally an amount of transition metal of 1 to 100 ppm, preferably 2 to 30 ppm, based on the octene used, is employed. Very particularly, rhodium or cobalt is used in an amount of 2 to 30 ppm, preferably of 5 to 10 ppm, based in each case on the octene used.

In the reaction of octene with hydrogen and carbon monoxide to give isononanal by the unmodified variant, appropriately relatively high pressures in the range from 5 to 70 MPa, preferably from 5 to 60 MPa and especially from 10 to 30 MPa are employed. Suitable reaction temperatures vary within the range from 50 to 180° C., preferably from 50 to 150° C. and especially from 100 to 150° C.

The composition of the synthesis gas, i.e. the proportions of carbon monoxide and hydrogen in the gas mixture, may vary within wide limits. In general, mixtures in which the molar ratio of carbon monoxide to hydrogen is 5:1 to 1:5 are used. Typically, this ratio is 1:1 or differs only slightly from this value. The olefinic compound can be supplied to the reaction zone as such or in solution. Suitable solvents are ketones such as acetone, methyl ethyl ketone, acetophenone, lower aliphatic nitriles such as acetonitrile, propionitrile or benzonitrile, dimethylformamide, linear or branched saturated aliphatic monohydroxyl compounds such as methanol, ethanol, propanol and isopropanol, aromatic hydrocarbons such as benzene or toluene, and saturated cycloaliphatic hydrocarbons such as cyclopentane or cyclohexane.

The hydroformylation stage can be performed either batchwise or continuously. The desired aldehydes are obtained from the crude hydroformylation product by conventional processes, for example by distillation. Isononanal and further volatile components are drawn off as top products and subjected to further fine purification if required.

The amounts of transition metal used are obtained in the distillation residue and, optionally after addition of fresh transition metal compound and withdrawal of a portion of the aldehyde condensation products formed in the course of the reaction, are recycled into the reaction zone.

The resulting mixture of isomeric isononanals is purified, appropriately by distillation, and then converted by oxidation to the corresponding isononanoic acid, preferably by oxidation in the liquid phase, although other process configurations such as oxidation in the gas phase are not ruled out. Suitable oxidizing agents are customary compounds suitable for oxidation of aliphatic aldehydes, such as oxygen, oxygen-containing gas mixtures, ozone, ozone-containing gas mixtures, peroxides, peracids, metal salts of peracids or transition metals in high oxidation states, for example potassium permanganate or manganese dioxide. Owing to good availability, the oxidizing agents used are appropriately molecular oxygen or gas mixtures comprising molecular oxygen. Further constituents of such gas mixtures are inert gases, for example nitrogen, noble gases and carbon dioxide. The proportion of the inert constituents of the oxygen-containing gas mixture is up to 90% by volume, especially 30 to 80% by volume. The preferred oxidizing agents are oxygen or air.

The oxidation can be performed either with addition of catalysts or in the absence of catalysts. Suitable catalysts are transition metals or compounds of transition metals which can be added in small amounts, for example from 0.1 to 5 ppm, calculated as the transition metal and based on the aldehyde used, such as titanium, vanadium, chromium, molybdenum, manganese, iron, cobalt, nickel, ruthenium, rhodium, palladium or copper. Such a process regime is described, for example, in DE 100 10 771 C1 or DE 26 04 545 A1.

It is likewise possible to perform the conversion in the presence of alkali metal or alkaline earth metal salts of weak acids. Especially in the case of oxidation of α-branched aldehydes in which the carbon atom adjacent to the carbonyl carbon atom bears the branch, the prior art recommends the presence of small amounts of alkali metal carboxylates to improve selectivity (DE 950 007, DE 100 10 771 C1). It is also possible to use a combination of alkali metal or alkaline earth metal carboxylates with transition metal compounds, as discussed in EP 1 854 778 A1.

In the oxidation of isononanal, which is prepared by the process according to the invention proceeding from 2-ethylhexanol via the dehydration and hydroformylation of the corresponding octene, the presence of alkali metal or alkaline earth metal carboxylates is advisable, generally in an amount of 1 to 30 mmol, preferably of 1 to 15 mmol and especially of 1 to 8 mmol per mole of aldehyde, calculated as the alkali metal or alkaline earth metal.

It is not necessary to use the alkali metal or alkaline earth metal carboxylates as a single compound. It is likewise possible to use mixtures of these compounds, although it is appropriate to use isononanoates. Preference is given, however, to using single compounds, for example lithium isononanoate, potassium isononanoate, sodium isononanoate, calcium isononanoate or barium isononanoate.

In general, a solution comprising alkali metal or alkaline earth metal isononanoates is prepared by neutralizing an aqueous solution comprising the alkali metal or alkaline earth metal compound with an excess of isononanoic acid, and this solution is added to the isononanal to be oxidized. Suitable alkali metal or alkaline earth metal compounds are particularly the hydroxides, carbonates or hydrogencarbonates.

However, it is also possible to obtain the alkali metal or alkaline earth metal isononanoates in the reaction mixture by adding alkali metal or alkaline earth metal compounds which are converted to the isononanoates under the reaction conditions. For example, it is possible to use alkali metal or alkaline earth metal hydroxides, carbonates, hydrogencarbonates or oxides in the oxidation stage. They can be added either in solid form or as an aqueous solution.

The reaction with the oxidizing agent, preferably with oxygen or oxygen-containing gases, is conducted within a temperature range from 20 to 100° C. Preference is given to working between 20 and 80° C., especially between 40 and 80° C. The temperature regime, constant or variable temperature, can be adapted to the individual requirements of the starting material and the reaction conditions.

The conversion of the reactants is preferably effected under atmospheric pressure. However, the use of elevated pressure is not ruled out. It is customary to work within a range from atmospheric pressure to 1.5 MPa, preferably at atmospheric pressure to 0.8 MPa.

The reaction time required for conversion of the isononanal to the corresponding isononanoic acid depends upon factors including the reaction temperature and the ratio of the reactants to one another. It is normally 30 minutes to 20 hours, especially 2 to 8 hours.

Isononanal can be used as such or dissolved in a solvent which is inert under the reaction conditions. Examples of suitable solvents are ketones such as acetone, esters, for example ethyl acetate, hydrocarbons, for example toluene, and nitrohydrocarbons such as nitrobenzene. The concentration of the aldehyde is limited by the solubility thereof in the solvent.

The oxidation step can be performed batchwise or continuously. Recycling of unconverted reaction participants is possible in both cases.

The isononanoic acid obtained proceeding from 2-ethylhexanol is a mixture of positionally isomeric aliphatic C9 monocarboxylic acids with α-unbranched and singly branched isononanoic acids as main components.

According to the gas chromatography analysis to DIN 51405 (area %), the main components present are 4-methyloctanoic acid, 6-methyloctanoic acid, 2,5-dimethylheptanoic acid, 2,3-dimethylheptanoic acid, 3-ethylheptanoic acid, 2-ethylheptanoic acid and 2-ethyl-4-methylhexanoic acid, and also small amounts of 2-propyl-3-methylpentanoic acid and 2-methyloctanoic acid. Small amounts of n-nonanoic acid are likewise present.

The isononanoic acid prepared by the process according to the invention is characterized in that the main components 4-methyloctanoic acid, 6-methyloctanoic acid, 2,5-dimethylheptanoic acid, 2,3-dimethylheptanoic acid, 3-ethylheptanoic acid, 2-ethylheptanoic acid and 2-ethyl-4-methylhexanoic acid make up a total amount of at least 80 mol %, based on the total content of positionally isomeric aliphatic C9 monocarboxylic acids.

From the crude acid mixture obtained after the oxidation, the pure isononanoic acid is obtained by means of distillation under customary conditions. The distillation residue containing the alkali metal or alkaline earth metal isononanoates and possibly transition metals is removed and can be fed back to the input aldehyde, optionally after addition of fresh alkali metal or alkaline earth metal isononanoates or alkali metal or alkaline earth metal compounds which are converted to the isononanoates under the reaction conditions, and optionally of fresh transition metal compounds.

In a proven embodiment of the process according to the invention, isononanal is initially charged in a suitable reactor, for example in a tubular reactor which has been provided with an inflow tray and optionally also contains random packings, and the oxygen or the oxygen-containing gas mixture is passed through the aldehyde from the bottom.

According to a further embodiment, the reactor used is a trickle tower containing random packings. The aldehyde is allowed to trickle downwards through the packing, and oxygen or an oxygen-containing gas mixture is simultaneously introduced into the tower in cocurrent or countercurrent.

The isononanoic acid prepared by the process according to the invention is subsequently esterified with alcohols to give carboxylic esters.

The direct esterification of alcohols with carboxylic acids is one of the basic operations of organic chemistry and is discussed, for example, in DE 10 2009 048 771 A1, DE 10 2009 048 772 A2 or DE 199 40 991 A. In order to increase the reaction rate, one of the reactants is used in excess and the water formed in the course of the reaction is removed in order to shift the equilibrium in accordance with the law of mass action to the side of the reaction product, i.e. of the carboxylic ester. According to the position of the boiling points of the reaction components, the isononanoic acid or the alcohol is used in excess. Typically, the more volatile component which is used in excess is removed from the reaction vessel together with the water of reaction and is passed into a downstream phase separator in which the organic phase separates from the aqueous phase, which is discharged from the process. The more volatile component may also form an azeotrope with water under the reaction conditions and may be capable of removing the water of reaction as an azeotroping agent. Other methods employed for removing the water of reaction are azeotropic distillation in the presence of a water-immiscible solvent such as hex-1-ene, cyclohexane or toluene, the heating of the reaction mixture while passing through an inert gas, and the conversion of the alcohol and isononanoic acid starting materials under reduced pressure or in the presence of a desiccant. It is advisable to equip the reaction vessel with a fractionating column having 2 to 10 theoretical plates in order to split the mixture of water and volatile reaction component which is removed from the reaction vessel in a water-depleted fraction which flows back into the reaction vessel and a water-enriched fraction which is removed as the top fraction.

The esterification of the isononanoic acid with alcohols can be performed without using a catalyst. This variant of the reaction has the advantage that it avoids feeding to the reaction mixture extraneous substances which can lead to unwanted contamination of the carboxylic ester. However, it is then generally necessary to maintain higher reaction temperatures because only in this way is it assured that the reaction proceeds at a sufficient, i.e. economically acceptable, rate. It should be noted in this context that the increase in the temperature can lead to thermal damage to the carboxylic ester. Therefore, it is not always possible to avoid the use of a catalyst which facilitates the reaction and increases the reaction rate. Frequently, the catalyst may be an excess of the isononanoic acid which is simultaneously a reaction component for the alcohol, such that the reaction proceeds autocatalytically. In addition, the customary esterification catalysts are suitable for influencing the reaction rate, such as sulphuric acid, formic acid, polyphosphoric acid, methanesulphonic acid or p-toluenesulphonic acid, and likewise combinations of such acids. It is likewise possible to use metallic catalysts such as catalysts containing titanium, zirconium or tin, for example the corresponding alkoxides or carboxylates. It is also possible to use catalytically active compounds which are solid under reaction conditions and are insoluble in the reaction system, such as alkali metal or alkaline earth metal hydrogensulphates, for example sodium hydrogensulphate. After the esterification has ended, solid catalysts are removed from the reaction mixture by simple filtration. The amount of catalyst used may extend over a wide range. It is possible to use between 0.001% by weight and 5% by weight of catalyst, based on the reaction mixture. However, since greater amounts of catalyst give rise to barely any advantages, the catalyst concentration is typically 0.001 to 1.0% and preferably 0.01 to 0.5% by weight, based in each case on the reaction mixture.

It is likewise possible to perform the esterification reaction in the presence of an adsorbent. This involves using porous, large-surface area, solid materials which are typically used in chemical practice both in the laboratory and in industrial plants. Examples of such materials are high-surface area polysilicic acids such as silica gels (silica xerogels), silica gel, kieselguhr, high-surface area aluminas and alumina hydrates, mineral materials such as clays, carbonates or activated carbon. Activated carbon has been found to be particularly useful. In general, the adsorbent is finely suspended in the reaction solution, which is moved by vigorous stirring or by introduction of an inert gas. This achieves intimate contact between the liquid phase and the adsorbent. The mass ratio of liquid phase to adsorbent can be set substantially freely and thus in accordance with the individual requirements. It has been found to be useful to use 0.05 to 30, preferably 0.1 to 5 and especially 0.1 to 1 parts by weight of adsorbent per 100 parts by weight of liquid phase. After conversion has ended, the adsorbent can be removed from the process and recycled into the esterification vessel and reused. Reuse is possible until the decolorizing power of the adsorbent is exhausted. However, it is also possible to leave the adsorbent in the crude product and to remove it at any appropriate stage during the workup process.

The reaction mixture obtained after conversion has ended comprises, as well as the carboxylic ester as the desired reaction product, possibly unconverted feedstocks, especially the reactant used in excess, and is worked up by known processes.

After removal of unconverted and excess starting materials, the crude ester obtained is subjected to a treatment with steam, which can be effected, for example, in a simple form by introduction of steam into the crude product. One advantage of steam treatment is that catalyst still present is destroyed in the course thereof and converted to hydrolysis products which can be filtered off efficiently. If the esterification reaction is performed in the presence of an adsorbent, the adsorbent already present facilitates the deposition of the catalyst conversion products. Otherwise, it may be advantageous to add an adsorbent at the start of steam treatment. The presence of an adsorbent during steam treatment likewise has an advantageous effect on the colour and colour stability of the carboxylic ester. However, it is also possible to filter off the adsorbent after the esterification reaction has ended and excess starting compounds have been removed, i.e. prior to performance of the steam distillation.

The steam treatment is optionally followed, after filtration of the adsorbent and further solids obtained, by the drying of the carboxylic ester, for example by passing an inert gas through the product at elevated temperature. It is also possible to simultaneously apply a reduced pressure at elevated temperature, and optionally to pass an inert gas through the product. It is also possible to blow dry water vapour through the carboxylic ester under reduced pressure. Even without the action of an inert gas, it is possible to work only at elevated temperature or only at relatively low pressure. Thereafter, the crude ester is filtered, if this has not yet been done, in order to free it of the solids, the hydrolysis products of the catalyst and the adsorbent, if added in the esterification stage or prior to the steam treatment. In general, the desired carboxylic ester is obtained as the residue during the drying stage. In particular cases, a fractional distillation under reduced pressure may follow.

Irrespective of whether an adsorbent was already present in the esterification stage and has already been filtered off at the start of the workup measures or only after the drying, it may be found to be appropriate to subject the carboxylic ester to another aftertreatment with an absorbent or to treat it with an oxidizing agent, for example with an aqueous peroxide solution or with ozone or ozone-containing gases, in order to improve the colour number.

At suitable points in the workup process, the crude ester can likewise be treated with an alkaline reagent, for example with an aqueous sodium hydroxide or sodium carbonate solution, for example after removal of the excess starting compounds and prior to the measure of steam distillation or during the steam distillation. It is also possible to add a portion of alkaline reagent after removal of the excess starting compounds, and the residual amount over the course of steam distillation. In this way, the acid number of the carboxylic ester can be adjusted according to the specification requirements.

The alcohols used as starting materials for the esterification stage are mono- or polyhydric alcohols which generally satisfy the general formula (I)

$$R(OH)_n \quad (I)$$

in which R is an aliphatic, cycloaliphatic or aromatic hydrocarbyl radical having 1 to 20 and preferably 2 to 10 carbon atoms, and n is an integer from 1 to 8, preferably 1, 2, 3, 4, 5 or 6.

Suitable alcohols are, for example, the monohydric alcohols propanol, isobutanol, n-butanol, n-hexanol, n-heptanol, 2-ethylhexanol, n-octanol, 3,5,5-trimethylhexanol, isononanol, n-nonanol or benzyl alcohol, the dihydric alcohols ethylene glycol, 1,2-propanediol, 1,3-propanediol, 1,3-butanediol, 2,3-butanediol, 1,4-butanediol, neopentyl glycol, 2,2-dimethylolbutane, 2,2,4-trimethylpentane-1,3-diol, 1,5-pentanediol, 1,2-hexanediol, 1,6-hexanediol, ethylene glycol or 3(4),8(9)-bishydroxymethyl-tricyclo[5.2.1.0$^{2,6}$]decane, the trihydric alcohols trimethylolethane, trimethylolpropane, trimethylolbutane, glycerol, and the tetrahydric alcohol pentaerythritol.

It is likewise possible for the isononanoic acid prepared in accordance with the invention to be reacted with glycidyl alcohol to form the glycidyl ester.

Suitable alcohols are likewise polyhydric alcohols or polyols having an ether group of the general formula $$H—(—O—[—CR^1R^2—]_m—)_o—OH \quad (II)$$

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer from 1 to 10, preferably 1 to 8 and especially 1, 2, 3 or 4, o is an integer from 2 to 15, preferably 2 to 8 and especially 2, 3, 4 or 5.

Suitable polyhydric alcohols of the general formula (II) containing an ether group are, for example, ditrimethylolpropane, dipentaerythritol, diethylene glycol, triethylene glycol, tetraethylene glycol, dipropylene glycol, tripropylene glycol or tetrapropylene glycol.

Depending on the boiling points of the alcohols used in relation to the boiling point of the isononanoic acid, the less volatile reaction component is used in deficiency and, in relation thereto, the more volatile reaction component is used in a 10 to 50% molar and preferably in a 20 to 40% molar excess per mole of functional group to be esterified. In the esterification of high-boiling polyhydric alcohols such as neopentyl glycol, trimethylolpropane, ditrimethylolpropane, pentaerythritol, dipentaerythritol, triethylene glycol or tetraethylene glycol, isononanoic acid is appropriately used in excess, this being removable in a simple manner by distillation from the crude ester. If, in contrast, low-boiling alcohols such as n-propanol or isobutanol are esterified with the isononanoic acid, the corresponding alcohol is reacted in excess.

The esterification reaction can be performed either batchwise or continuously.

The inventive esters are outstandingly suitable as plasticizers for all common high-polymeric thermoplastic polymers. They are likewise of excellent usability as lubricants. For production of lubricants, isononanoic acid is frequently esterified in a mixture with other monocarboxylic acids. For example, a mixture comprising isononanoic acid, n-pentanoic acid and n-heptanoic acid is reacted with polyhydric alcohols.

The examples which follow describe the preparation of isononanoic acid proceeding from 2-ethylhexanol and the preparation of carboxylic esters.

EXAMPLES

I. Dehydration of 2-Ethylhexanol

For dehydration, a quartz tube having a length of 1.3 meters and a diameter of 0.03 meter was used, in which the heated zone extended over 1.1 meters. The quartz tube was charged with 250 ml of the acidic catalyst Al 3996 from BASF SE in the form of tablets of size 3×3 millimeters. The dead volume was filled with glass rings.

2-Ethylhexanol was evaporated in an upstream evaporator and conducted with the aid of a nitrogen stream at standard pressure over the catalyst bed at a temperature of 350° C. and with a space velocity of 0.5 liter per liter of catalyst volume and hour. The reaction mixture obtained was condensed in a downstream collecting vessel and the aqueous phase was removed. The organic phase obtained had the following composition determined by gas chromatography (area %, to DIN 51405):

| Forerun/C4-C7 hydrocarbons | 0.3 |
|---|---|
| Other C8 olefins | 9.6 |
| 2-ethyl-1-hexene | 7.6 |
| cis-3-methyl-3-heptene | 14.6 |
| trans-3-methyl-3-heptene | 28.8 |
| cis-3-methyl-2-heptene | 16.2 |
| trans-3-methyl-2-heptene | 23.9 |
| n-octenes | 0.8 |
| Final fraction | 0.1 |

II. Hydroformylation of the Octene Obtained in Step I

The crude octene obtained in step I was hydroformylated in the presence of 5 ppm of rhodium, added in the form of a solution of rhodium 2-ethylhexanoate in 2-ethylhexanol and based on octene input, at a temperature of 140° C. and a synthesis gas pressure of 19 MPa over a period of three hours. The molar composition of the synthesis gas was 1 mol of hydrogen to 1 mol of carbon monoxide. The crude hydroformylation product obtained had the following composition determined by gas chromatography (area %, to DIN 51405):

| Forerun | 0.1 |
|---|---|
| C8 hydrocarbons | 8.5 |
| Intermediate fraction | 0.2 |
| Isononanal | 88.1 |
| n-nonanal | 1.4 |
| Final fraction | 1.7 |

The results of further hydroformylation experiments with octene obtained via the dehydration of 2-ethylhexanol are compiled in Table 1 below. Before use, the crude octene was distilled in a Claisen distillation system to remove the final fraction at a top temperature of 119-122° C. and at standard pressure. The input octenes and the reaction products obtained were analysed by gas chromatography (figures in area %, to DIN 51405).

TABLE 1

Hydroformylation of octenes obtained by 2-ethylhexanol dehydration

| Example | IIa | IIb |
|---|---|---|
| Reactant input | distilled | distilled |
| GC analysis of reactant (%) | | |
| Forerun/C4-C7 hydrocarbons | 0.3 | 0.4 |
| Other C8 olefins | 5.9 | 7.7 |
| 2-ethyl-1-hexene | 9.3 | 9.2 |
| cis-3-methyl-3-heptene | 15.2 | 15.0 |
| trans-3-methyl-3-heptene | 27.4 | 27.1 |
| cis-3-methyl-2-heptene | 16.1 | 15.6 |
| trans-3-methyl-2-heptene | 25.2 | 24.7 |
| n-octenes | 0.5 | 0.2 |
| Final fraction | 0.1 | 0.1 |
| Experimental conditions | | |
| Rh concentration [ppm], based on octene input | 20 | 10 |
| Pressure [MPa] | 19 | 27 |
| Temperature [° C.] | 140 | 140 |
| Reaction time [h] | 2 | 2 |
| GC analysis of product (%) | | |
| Forerun | 0.1 | 0.1 |
| C8 hydrocarbons | 2.5 | 1.1 |
| Intermediate fraction | 0.3 | 0.1 |
| isononanals | 90.8 | 94.7 |
| n-nonanal | 2.0 | 1.4 |
| Final fraction | 4.3 | 2.6 |

The hydroformylation experiments conducted using triphenylphosphine as complex ligand with the octene obtained via the dehydration of 2-ethylhexanol are compiled in Table 2 below. Undistilled material was used. The input octenes and the reaction products obtained were analysed by gas chromatography (figures in area %, to DIN 51405).

TABLE 2

Hydroformylation of octenes, obtained by the 2-ethylhexanol dehydration, addition of triphenylphosphine

| Example | IIc | IId | IIe | IIf |
|---|---|---|---|---|
| Reactant input | undistilled, crude | undistilled, crude | undistilled, crude | undistilled, crude |
| GC analysis of reactant (%) | | | | |
| C4-C7 hydrocarbons | 0.3 | 0.3 | 0.3 | 0.4 |
| Other C8 olefins | 19.1 | 19.1 | 19.1 | 11.6 |
| 2-ethyl-1-hexene | 7.9 | 7.9 | 7.9 | 8.6 |
| 3-methyl-3-heptene | 36.5 | 36.5 | 36.5 | 40.0 |
| 3-methyl-2-heptene | 36.2 | 36.2 | 36.2 | 39.3 |
| Final fraction | <0.01 | <0.01 | <0.01 | <0.1 |
| Experimental conditions | | | | |
| Rh concentration [ppm], based on octene input | 10 | 10 | 10 | 10 |
| Equivalents of TPP | 3 | 50 | 100 | 3 |
| Pressure [MPa] | 18 | 27 | 18 | 14 |
| Temperature [° C.] | 140 | 140 | 140 | 160 |
| Reaction time [h] | 1 | 2 | 1 | 2 |
| GC analysis of product (%) | | | | |
| Forerun | 0.1 | 0.1 | 0.1 | 0.1 |
| C8 hydrocarbons | 52.2 | 70.9 | 81.7 | 14.1 |
| Intermediate fraction | 0.8 | 0.1 | 0.1 | 1.9 |
| isononanals | 45.7 | 28.3 | 17.6 | 76.1 |
| n-nonanal | 0.5 | 0.1 | 0.1 | 0.5 |
| Final fraction | 0.7 | 0.4 | 0.4 | 7.3 |

III. Oxidation of the Isononanal Obtained in Step II. To Isononanoic Acid

From the isononanal obtained in Example IIa, low boilers and unconverted olefin as the top product were first removed in a 24-tray column at 200 hPa, a bottom temperature of 120° C. and a reflux ratio of 2:1. After low boiler removal, the bottom temperature was raised to 140-150° C. and the isononanal was drawn off overhead (boiling point at 100 hPa: 110-113° C.), while high boilers remained in the distillation bottoms.

The isononanal obtained had the composition determined by gas chromatography which follows and the parameters which follow, and was used for the subsequent liquid phase oxidation.

TABLE 3

Gas chromatography analysis (area %, to DIN 51405) of isononanal proceeding from 2-ethylhexanol

| | |
|---|---|
| Forerun/C8 hydrocarbons | 0.2 |
| Intermediate fraction | 0.4 |
| 2-ethyl-4-methylhexanal | 10.8 |
| 2-propyl-3-methylpentanal | 3.6 |
| 2,5-dimethylheptanal | 21.9 |
| 2,3-dimethylheptanal (isomer) | 4.8 |
| 2,3-dimethylheptanal (isomer) + 2-ethylheptanal | 8.4 |
| 2-methyloctanal | 1.7 |
| 3-ethylheptanal | 10.4 |
| 4-methyloctanal | 20.6 |
| 4,5-dimethylheptanal | 0.6 |
| 6-methyloctanal | 11.0 |
| Other i-nonanals | 1.8 |
| n-nonanal | 0.9 |
| Final fraction | 2.9 |

TABLE 4

Parameters of the isononanal proceeding from 2-ethylhexanol

| Parameter/unit | DIN/ASTM | Value |
|---|---|---|
| $V_{20}$ (mm$^2$/s) | ASTM D 445 | 1.536 |
| $V_{40}$ (mm$^2$/s) | | 1.179 |
| Solidification point (° C.) | | −100 |
| $d^{20/4}$ (g/cm$^3$) | DIN 51757, | 0.827 |
| $d^{50/4}$ (g/cm$^3$) | Method D/ASTM D 4052 | 0.811 |
| $n^{20/D}$ | DIN 51423-2/ | 1.424 |
| | ASTM D 1747 | |
| CO number (mg KOH/g) | DIN 53173 | 339/349 |
| Flashpoint (° C.) | DIN EN ISO 2719 | 60 |
| Platinum/cobalt Hazen colour number | DIN EN ISO 6271/ ASTM D 1209 | 15 |

The liquid phase oxidation of the isononanal to isononanoic acid was effected without addition of solvent in a bubble column reactor at 50° C. with pure oxygen at standard pressure over a period of 6 hours. A 50% by weight aqueous solution of potassium hydroxide was added to the input aldehyde in such an amount that 50 mmol of potassium were present per mole of isononanal.

The crude acid obtained was subsequently distilled in a 4.5-tray column at a bottom temperature of 148 to 159° C. and at a top temperature of 136-139° C. at 20 hPa. Low boilers and unconverted aldehyde were removed as the forerun fraction, and high boilers remained in the distillation residue. The distillation yield of isononanoic acid was 84.7% with a purity determined by gas chromatography of 98.8%.

The resulting isononanoic acid had the following composition determined by gas chromatography to DIN 51405 (area %):

TABLE 5

Gas chromatography analysis of the isononanoic acid proceeding from 2-ethylhexanol (area %, to DIN 51405)

| | |
|---|---|
| Forerun | 0.4 |
| 2-ethyl-4-methylhexanoic acid | 9.3 |
| 2-propyl-3-methylpentanoic acid | 3.0 |
| 2,5-dimethylheptanoic acid + 2,3-dimethylheptanoic acid (isomer) | 25.7 |
| 2,3-dimethylheptanoic acid (isomer) | 8.4 |
| 3-ethylheptanoic acid + 2-ethylheptanoic acid | 12.9 |
| 2-methyloctanoic acid | 0.8 |
| 4-methyloctanoic acid | 20.9 |
| 6-methyloctanoic acid | 12.3 |
| n-nonanoic acid | 0.3 |
| Other i-nonanoic acids | 5.2 |
| Final fraction | 0.8 |

The parameters determined for the isononanoic acid are compiled in Table 6.

TABLE 6

Parameters of isononanoic acid proceeding from 2-ethylhexanol

| Parameter/unit | DIN/ASTM | Value |
|---|---|---|
| $V_{20}$ (mm$^2$/s) | ASTM D 445 | 10.68-11.18 |
| $V_{40}$ (mm$^2$/s) | | 5.83-5.88 |
| $V_{50}$ (mm$^2$/s) | | 4.50 |
| $d^{20/4}$ (g/cm$^3$) | DIN 51757, | 0.906-0.907 |
| $d^{40/4}$ (g/cm$^3$) | Method D/ | 0.891 |
| $d^{50/4}$ (g/cm$^3$) | ASTM D 4052 | 0.883-0.884 |

TABLE 6-continued

Parameters of isononanoic acid proceeding from 2-ethylhexanol

| Parameter/unit | DIN/ASTM | Value |
|---|---|---|
| $n^{20/D}$ | DIN 51 423-2/ ASTM D 1747 | 1.432-1.433 |
| Solidification point (° C.) | | −81 |
| Boiling point (° C.) at 1013 hPa | DIN 53171/ ASTM D 1078 | 241-242 |
| Acid number mg KOH/g | DIN EN ISO 2114/ ASTM D 1613 | 351 |
| Flashpoint (° C.) | DIN EN ISO 2719 | 129 |
| Platinum/cobalt Hazen colour number | DIN EN ISO 6271/ ASTM D 1209 | 7 |

IV. Esterification of Isononanoic Acid Obtained in Step III

The esterification of polyols with the isononanoic acid prepared in step III was performed in a heatable 2 l four-neck flask which was equipped with stirrer, internal thermometer and a water separator.

The flask was initially charged with the polyol and the carboxylic acid in a 20 mol % excess, based on each alcohol group to be esterified, and, depending on the batch, 0.05 mol % of tetra(isopropyl) orthotitanate, based on the polyol. In examples IV/2, IV/6 and IV/7, no catalyst was employed. The carboxylic acid present had autocatalytic action. In examples IV/1 to IV/6, the esterification reaction was performed in the presence of activated carbon. In examples IV/6 and IV/7, a mixture of isononanoic acid, n-pentanoic acid and n-heptanoic acid was used. The polyols used, the esterification conditions and the conditions employed in the workup of the crude ester are compiled in Table 7 below.

While stirring and with application of the reduced pressure specified, the mixture was heated to 200° C. and water of reaction formed was removed on the water separator. After a reaction time of 2 hours at this stage, the pressure was lowered to 600 hPa and the temperature increased to 220° C. The reaction profile was monitored by continuous weighing of the water of reaction discharged via the water separator and by sampling and gas chromatography analysis of the samples. Another lowering of the reduced pressure down to 300 hPa was undertaken depending on the degree of esterification. In the case of an ester content determined by gas chromatography of at least 98.0%, the reaction was ended by cooling the mixture. The respective esterification time can be found in Table 7.

From the reaction mixtures obtained in Examples IV/1-IV/7, the excess unconverted carboxylic acid was first removed. There followed a steam distillation and subsequent drying. After filtration of the activated carbon added at standard pressure and room temperature, the residue obtained was a light-coloured polyol ester with the composition determined by gas chromatography (area % to DIN 51405) reported in Table 7, and the parameters measured.

TABLE 7

Esterification of the isononanoic acid prepared in step III proceeding from 2-ethylhexanol with polyols

| | | 1 | 2 | 3 | 4 | 5 | 6 | 7 |
|---|---|---|---|---|---|---|---|---|
| Esterification | | | | | | | | |
| Polyol | | TEG | NPG | 1,3 BG | TCD | TMP | pentaerythritol | Dipentaerythritol |
| Amount of polyol | mol | 0.67 | 0.66 | 1.00 | 1.0 | 1.00 | 0.45 | 0.29 |
| Isononanoic acid | mol | 1.73 | 1.72 | 2.60 | 2.60 | 3.60 | 0.76 | 0.66 |
| n-heptanoic acid | mol | | | | | | 0.73 | 0.71 |
| n-pentanoic acid | mol | | | | | | 0.72 | 0.77 |
| Activated carbon | g | 1.0 | 0.7 | 0.9 | 2.7 | 2.18 | 2.55 | — |
| Tetra(isopropyl) orthotitanate | mg | 220 | | 90 | 90 | 70 | | |
| Reaction time | h | 6 | 8 | 6 | 10 | 17 | 10 | 10 |
| Reaction temperature | °C. | 220 | 220 | 220 | 220 | 220 | 220 | 220 |
| Reaction pressure | hPa | 600-400 | 600-300 | 600-400 | 1013-400 | 600-400 | 1013-400 | 1013-400 |
| Carboxylic acid removal | | | | | | | | |
| Temperature | °C. | 120-226 | 105-200 | 120-198 | 140-200 | 100-220 | 120-210 | 120-220 |
| Pressure | hPa | 1 | 1.2 | 2 | 3 | 2 | 3 | 3 |
| Steam distillation | | | | | | | | |
| Time | min | | 120 | | 105 | 105 | 105 | 105 |
| Temperature | °C. | | 180 | | 180 | 160 | 180 | 180 |
| Drying | | | | | | | | |
| Time | min | | 30 | | 30 | 30 | 30 | 30 |
| Temperature | °C. | | 140 | | 140 | 140 | 140 | 140 |
| Pressure | hPa | | 2 | | 2 | 2 | 2 | 2 |
| Polyol | | TEG | NPG | 1,3 BG | TCD | TMP | pentaerythritol | dipentaerythritol |
| Gas chromatography analysis (%) | | | | | | | | |
| Acid | | 0.1 | 0.1 | 0.1 | 0.3 | 0.1 | 0.1 | 0.1 |
| Partial ester | | 1.3 | 0.4 | 0.4 | 1.2 | 1.2 | 0.11 | 0.5 |
| Full ester | | 98.4 | 99.1 | 99.2 | 98.0 | 98.5 | 99.2 | 98.8 |
| Final fraction | | 0.2 | 0.4 | 0.3 | 0.5 | 0.2 | 0.6 | 0.6 |
| Parameters | | | | | | | | |
| VN DIN/ENISO 3681 | mg KOH/g | 258 | 284-287 | | 224-227 | 302-303 | 377-387 | 368-370 |
| $V_{20}$ ASTM D 445 | mm$^2$/s | 21.00 | 19.53-19.75 | 15.30 | 134.30 | 64.16 | 58.19 | 170.8-172.6 |
| $V_{40}$ | mm$^2$/s | | 9.41-9.43 | 7.77 | 45.2 | 24.96 | 24.28 | 62.3-62.5 |
| $V_{50}$ | mm$^2$/s | 7.72 | 7.01 | 5.92 | 29.30 | 16.82 | | 41.39 |
| $d^{20/4}$ DIN 51757, Method D/ASTM D 4052 | g/cm$^3$ | 0.9638 | 0.915-0.917 | 0.918 | 0.976 | 0.9415 | 0.9814 | 0.998 |
| $d^{40/4}$ | g/cm$^3$ | | | 0.903 | 0.962 | 0.927 | 0.9664 | 0.983-0.984 |
| $d^{50/4}$ | g/cm$^3$ | 0.9383 | 0.895 | 0.896 | 0.955 | 0.9198 | | 0.977 |
| $n_{20/D}$ DIN 51 423-2/ASTM D 1747 | | 1.4488 | 1.445 | 1.443 | 1.476 | 1.453 | 1.453 | 1.457-1.458 |
| Solidification point | °C. | −69 | −71 | −75 | −51 | −59 | −63 | −53 |
| Flashpoint ISO2719 | °C. | >130 | >150 | >175 | >130 | >135 | >135 | >175 |

TEG—Triethylene glycol;
NPG—Neopentyl glycol;
TMP—Trimethylolpropane;
1,3 BG—1,3-butanediol;
TCD—3(4);8(9)-bishydroxymethyltricyclo[5.2.1.0$^{2,6}$]decane

The invention claimed is:

1. A process for preparing carboxylic esters of a mixture of structurally branched C9 monocarboxylic acids proceeding from 2-ethylhexanol, wherein (a) 2-ethylhexanol is dehydrated to an octene mixture in the presence of a catalyst;

(b) the octene mixture obtained in step a) is reacted in the presence of a transition metal compound of group VIII of the periodic table of the elements with carbon monoxide and hydrogen to give a mixture of isomeric isononanals;

(c) the mixture of isomeric isononanals obtained in step b) is oxidized to a mixture of structurally branched C9 monocarboxylic acids; and (d) the mixture of structurally branched C9 monocarboxylic acids obtained in step c) is reacted with alcohols to give carboxylic esters.

2. The process according to claim 1, wherein the catalyst used in step a) is alumina, nickel precipitated on alumina, or phosphoric acid precipitated on silica or alumina.

3. The process according to claim 1, wherein 2-ethylhexanol is dehydrated in the gas phase in step a).

4. The process according to claim 1, wherein the transition metal compound of group VIII of the periodic table of the elements used in step b) is a cobalt or rhodium compound.

5. The process according to claim 1, wherein the reaction in step b) is performed in the absence of complex-forming organophosphorous compounds.

6. The process according to claim 1, wherein the mixture of isomeric isononanals obtained in step b) is distilled.

7. The process according to claim 1, wherein the oxidation in step c) is effected in the presence of alkali metal or alkaline earth metal carboxylates.

8. The process according to claim 7, wherein the alkali metal or alkaline earth metal carboxylate used is lithium isononanoate, potassium isononanoate, sodium isononanoate, calcium isononanoate or barium isononanoate.

9. The process according to claim 1, wherein the mixture of isomeric isononanals is oxidized in the liquid phase in step c).

10. The process according to claim 1, wherein the mixture of isomeric isononanals is oxidized in step c) with oxygen or oxygen-containing gases provided to the mixture of structurally branched C9 monocarboxylic acids.

11. The process according to claim 1, wherein the reaction in step d) is performed in the presence of an adsorbent.

12. The process according to claim 1, wherein the reaction in step d) is performed in the presence of a catalyst.

13. The process according to claim 1, wherein the alcohols converted in step d) are of the general formula (I)

$$R(OH)_n \qquad (I)$$

in which R is an aliphatic, cycloaliphatic or aromatic hydrocarbyl radical having 1 to 20 carbon atoms, and n is an integer from 1 to 8.

14. The process according to claim 1, wherein the alcohols converted in step d) are of the general formula (II)

$$H\text{—}(\text{—}O\text{—}[\text{—}CR^1R^2\text{—}]_m\text{—})_o\text{—}OH \qquad (II)$$

in which $R^1$ and $R^2$ are each independently hydrogen or an alkyl radical having 1 to 5 carbon atoms, or a hydroxyalkyl radical having 1 to 5 carbon atoms, m is a number from 1 to 10, and o is an integer from 2 to 15.

15. The process according to claim 1, wherein the alcohol used in step d) is glycidyl alcohol.

16. The process according to claim 2, wherein 2-ethylhexanol is dehydrated in the gas phase in step a).

17. The process according to claim 2, wherein the transition metal compound of group VIII of the periodic table of the elements used in step b) is a cobalt or rhodium compound.

* * * * *